United States Patent
Haussmann (10) Patent No.: US 7,369,670 B2
(45) Date of Patent: May 6, 2008

(54) EARPLUG AND METHOD FOR MANUFACTURING THE SAME

(75) Inventor: Mathias Haussmann, Zurich (CH)

(73) Assignee: Phonak AG, Staefa (CH)

( * ) Notice: Subject to any disclaimer, the term of this patent is extended or adjusted under 35 U.S.C. 154(b) by 708 days.

(21) Appl. No.: 10/925,138

(22) Filed: Aug. 25, 2004

(65) Prior Publication Data
US 2006/0045297 A1 Mar. 2, 2006

(51) Int. Cl.
H04R 25/00 (2006.01)
(52) U.S. Cl. ............... 381/322; 29/896.21; 381/328
(58) Field of Classification Search ............ 381/322, 381/324, 325, 328; 29/896.21
See application file for complete search history.

(56) References Cited

U.S. PATENT DOCUMENTS

| | | | |
|---|---|---|---|
| 3,890,474 A | 6/1975 | Glicksberg | |
| 4,729,451 A | 3/1988 | Brander et al. | |
| 4,969,534 A | 11/1990 | Kolpe et al. | |
| 5,692,059 A | 11/1997 | Kruger | |
| 6,484,842 B1 | 11/2002 | Widmer et al. | |
| 6,533,062 B1 | 3/2003 | Widmer et al. | |
| 6,585,075 B1 | 7/2003 | Gauthier | |
| 2003/0112990 A1 | 6/2003 | McIntosh et al. | |
| 2003/0133583 A1 | 7/2003 | Widmer et al. | |

FOREIGN PATENT DOCUMENTS

| | | |
|---|---|---|
| DE | 2512343 A1 | 10/1976 |
| DE | 3719963 A1 | 3/1988 |
| DE | 4119615 A1 | 1/1992 |
| DE | 196 34 984 A1 | 3/1998 |
| DE | 100 41 733 A1 | 3/2002 |
| DE | 100 46 202 A1 | 3/2002 |
| EP | 0098421 A3 | 12/1986 |
| EP | 0455203 A2 | 11/1991 |
| WO | 89/12432 A1 | 2/1989 |
| WO | 02/17839 A1 | 3/2002 |
| WO | WO 02/17838 A1 | 3/2002 |
| WO | WO 02/071794 A1 | 9/2002 |

OTHER PUBLICATIONS

James M. Kates, A Computer Simulation of Hearing Aid Response and the Effects of Ear Canal Size, The Journal of the Acoustical Society of America, May 31, 1988, pp. 1952-1963, vol. 83, No. 5.
G. Szwoch et al., Computer Modeling of Acoustical Elements of a Hearing Aid, Dec. 31, 2001, pp. 1-14.
European Search Report Dated Jan. 10, 2008 Application No. EP 07 01 9149.

Primary Examiner—Suhan Ni
(74) Attorney, Agent, or Firm—David S. Safran (57) ABSTRACT

The invention relates to an active hearing protection earplug comprising a shell (2000) to be worn at least in part in a user's ear canal and being adapted to attenuate sound waves arriving at the outer end (2001) of the shell, and an active system (2002, 2010) comprising an input transducer (2024) for converting ambient sound into audio signals, an audio signal processing unit (2028) for processing said audio signals, and an output transducer unit (2010) mounted within the shell for converting said processed audio signals into sound output at the inner end of the shell, wherein the amplification of the active system is negative and wherein the output transducer unit comprises at least two separate outputs (2032, 2034). The invention also relates to a method for manufacturing such an earplug.

5 Claims, 4 Drawing Sheets

EARPLUG AND METHOD FOR MANUFACTURING THE SAME

BACKGROUND OF THE INVENTION

1. Field of the Invention

The present invention relates to earplugs serving as a hearing protection device or as a hearing aid. The earplug comprises a shell which is to be inserted at least in the outer part of the user's ear canal.

2. Description of Related Art

A large part of the population is exposed to hazardous noise from time to time. This can be at work, whilst traveling, during leisure activities or at home. The exposure can lead to permanent hearing loss, distract people's attention from other hazards or simply cause stress. In order to prevent both accidents and permanent hearing damage, hearing protection devices (HPDs) have been provided in many styles and over many years. It started with the earmuff which is still very relevant and addresses very noisy environments (e.g. airports, construction, shooting) or complex working/communication situations (e.g. fighter pilots). Over the years development of biocompatible soft materials has enabled soft earplugs in different styles and colors as well as recent development of "one fits many" standard semi-soft earplugs in silicon-rubber type materials. For severe situations even the combination of an earmuff and an "in-the-ear" HPD is required to achieve desired attenuation. The physical limitation of hearing protection based on ear worn devices is defined where bone-conduction (body acoustics) becomes dominant at around 40 dB attenuation.

A common disadvantage of the above mentioned HPD styles is wearing discomfort. In case of the earmuffs, they are large which creates difficulties in combination with other head worn gear and they "close off" the ear too much for most applications. The in-the-ear styles mentioned are devices made to fit "the average" ear in one way or the other. Either the fit is provided by softness of the material which leads to undefined device insertion and undefined attenuation, or the fit is provided by standard shaped structures intended to block off the ear canal. In both cases the flat distribution of the individual shape of the outer ear and the ear canal leads to bad fit, pressure points in the ear and undefined positioning of the device.

To address this wearing comfort issue, in-the-ear hearing aid technology has been applied making customized ear molds with passive acoustical filter. These are long lasting devices with good wearing comfort. However, this customization process is traditionally a very manual process creating varying results over time, low reproducibility and the quality is very operator skill dependent.

The fabrication of customized hard shells by use of a rapid prototyping technology, primarily for hearing aids is described, for example, in U.S. Pat. No. 6,533,062 B1 or U.S. 2003/0133583 A1.

The term "earplug" as used in the following should designate any object which comprises at least a portion which is to be worn at least in the outer portion of the user's ear canal in a manner that it is retained within the ear canal.

If an earplug is designed as an active hearing protection device or a hearing aid, it includes an electroacoustic output transducer (i.e. speaker or receiver) which converts audio signals into sound to be output at the inner (distal) end of the shell. The system further includes an electroacoustic input transducer (i.e. a microphone) which converts ambient sound into audio signals and an audio signal processing unit which may comprise, for example, an amplifier and electronic filters. In addition, the system comprises a power source (battery) which may be mounted at or within the shell. The microphone and the audio signal processing unit may be mounted at or within the shell or may be external to the earplug, with a wired or wireless connection to the output transducer being provided in the latter case.

If the earplug is designed as an active hearing protection device, the earplug provides for attenuation of ambient sound reaching the outer (proximal) end of the earplug, and the audio signal processing unit is designed such that the overall amplification is negative. In this case, the active components serve to temporarily or spectrally select the sound signals which should be perceived by the user, thereby by-passing the mechanical attenuation function.

If the earplug is designed as an in-the-ear hearing aid, the acoustical gain tends to be quite high, for example, up to 50 dB gain or 120 dB sound pressure level.

If the earplug is designed as a passive hearing protection device, it includes an acoustic filter element for attenuating sound received at the outer end of the earplug, but it does not include any active sound producing elements.

In general, an earplug may be made of a soft, resilient material in order to conform to the individual shape of the user's ear canal and outer ear.

In addition, it is known to measure or determine the inner shape of the user's ear canal and outer ear by producing an impression or by three-dimensional laser scanning and to produce an earplug with a shell having an outer surface which is individually shaped according to the user's ear canal and outer ear in order to improve wearing comfort and the retaining forces. Such individually shaped earplugs are commonly referred to as customized earplugs. Due to the improved fitting, the material of the shell of customized earplugs may be significantly harder than the material of standardized soft earplugs. One known method for producing the individually shaped shell is layer-by-layer laser sintering (selective laser sintering (SLS)) of an appropriate powder material such as polyamide, see for example U.S. Pat. No. 6,533,062 B1 or U.S. 2003/0133583 A1.

DE 196 34 984 A1 relates to a hearing aid having a multi-way output transducer which is located in a sound outlet passage of an earplug having an individual outer shape. The multi-way output transducer may comprise several identical or different electroacoustic transducers which are realized as a multi-layer foil transducer on a spiral band.

U.S. Pat. No. 5,692,059 relates to an active hearing protection device which comprises a microphone, an electroacoustic output transducer and an accelerometer for sensing vibrations. The device comprises a Y-shaped output tube with one of the branches being connected to the microphone and the other branch being connected to the output transducer.

U.S. Pat. No. 6,533,062 B1 relates to a customized earplug having a shell formed by selective laser sintering, which may form a hearing aid or a hearing protection device. The shell includes integrated venting channels and specifically shaped sound input tubes to the microphone. For the case of a hearing aid function it is described that these input tubes may comprise acoustic adapters in the form of specifically shaped lines or tubes which serve for tuning the acoustic impedance of the input tube. It is also described that venting channels may serve as acoustic conductors for acoustic impedance tuning. A similar disclosure is found in U.S. Pat. No. 6,484,842 B1. Further, these documents disclose that the outer part of the shell may be made of a softer material than the inner part, with the outer part comprising a cavity for receiving an electronic module including the output transducer which is held there by elastic forces.

WO 02/01794 A1 relates to a customized earplug comprising a shell made by SLS, which may serve as a hearing aid or a hearing protection device, with venting tubes and a sound channel being integrated within the shell.

DE 100 41 733 A1 relates to a customized hearing protection device earplug which may include an active version. It is described in this document that mechanical frequency tuning may be achieved by filter selection, by selection of a venting tube with variable diameter and by providing the outer end of the shell as a resonance cavity.

DE 100 46 202 A1 relates to a customized earplug into which an output transducer is integrated by being directly fixed to the shell in a corresponding cavity. The microphone for providing an audio signal to the output transducer is remote from the earplug.

Due to the relatively high amplification in hearing aids the output transducer has to be mechanically decoupled from the microphone in order to avoid feedback problems due to vibrations transmitted from the output transducer to the microphone. Therefore it is common to provide for a soft mounting of the output transducer within the shell, for example by embedding the output transducer in an elastic material, see, for example, U.S. Pat. No. 4,969,534 or U.S. Pat. No. 4,729,451.

U.S. Pat. No. 6,585,075 B1 relates to a hearing aid in which the output transducer is hard mounted to the shell. In order to compensate for the vibration of the output transducer, the portion of the shell at which the output transducer is mounted is surrounded with an energy adsorbing soft material.

U.S. 2003/0112990 relates to a hearing protection or hearing aid earplug consisting of a core element surrounded by sleeve which is filled with a curable rubber-like material having a hardness value of less than shore A-30 for individually adapting the earplug to the shape of the user's ear canal and outer ear. The core element comprises a first sound bore which extends through the earplug and which may be detachably connected at its proximal end with a remote measurement apparatus and a second sound bore which is parallel to the first sound bore and which may be closed by an attenuation element or may serve as sound input by a hearing aid unit.

It is one object of the invention to provide for an active hearing protection earplug which provides for an optimized sound output.

It is a second object of the invention to provide for a method for manufacturing an earplug with an output transducer, which provides for an optimized sound output.

It is a third object of the invention to provide for a customized active hearing protection earplug which can be assembled in an easy manner and which allows for a defined positioning of the output transducer.

It is a fourth object of the invention to provide for a hearing protection earplug which allows for external control of the operation of the hearing protection earplug when worn by the user, in particular in order to control the sound attenuation function.

It is a fifth object of the invention to provide for a hearing protection earplug which ensures, other than by electronic peak clipping means, that the sound pressure level at a sound outlet opening at the inner end of the earplug does not exceed a predefined threshold value.

SUMMARY OF THE INVENTION

The first object is achieved by an active hearing protection earplug as defined in claim 1. This solution is beneficial in that, by providing the output transducer unit mounted within the shell with at least two separate outputs, the output sound quality can be significantly improved compared to a single output transducer, since the multiple outputs together may form a wideband receiver/speaker which may allow even for high-fidelity applications.

Preferably each output is connected with a separate sound output tube which preferably is formed as a cavity integral within the shell, with the sound output tubes merging into a common sound outlet tube. Thereby a passive crossover network of an acoustic multi-way system may be formed for controlling mixing of the output signals of the different outputs. The acoustic parameters of this passive crossover network can be optimized by shaping and/or sizing the sound output tubes in a corresponding manner.

The second object is achieved by a manufacturing method as defined in claim 10. This solution is beneficial in that, by sizing the sound cavity downstream the output transducer unit according to an acoustic model of the earplug, the sound frequency response of the output transducer unit can be tuned in an easy and predictable manner for optimizing the sound output of the output transducer unit.

According to a preferred embodiment, the inner shape of the user's outer ear and ear canal is measured and the model is related to the earplug when worn by the user. Thereby the sound output of the output transducer unit can be optimized not only regarding the specific type of shell and output transducer unit used, but in addition regarding the individual ear of the user.

The third object is achieved by an active hearing protection earplug according to claim 15. This solution is beneficial in that, by hard mounting the output transducer unit within a predefined cavity within a hard shell, the provision of a resilient, soft material between the output transducer unit and the shell is avoided, so that the assembly process is simplified and the position of the output transducer unit relative to the shell is precisely and reliably defined.

The fourth object is achieved by a hearing protection earplug according to claim 19. This solution is beneficial in that, by providing the shell with a measurement channel formed as a cavity integral with the shell and extending from the outer end of the shell to the inner end or the interior of the shell, an acoustic connection between an external measurement unit and the user's ear canal or the interior of the shell can be achieved for measurement purposes even when the earplug is worn by the user. Thereby experimental control of the proper function of the hearing protection earplug when being worn by the user is enabled.

The fifth object is achieved by a hearing protection earplug according to claim 23. This solution is beneficial in that, by providing the sound passage of the earplug with a sound pressure level actuating closing means, the user's ear can be protected from excessive sound pressure levels in a simple manner.

Preferably, the closing means are formed integral with the shell. Further, the closing means may be arranged at an outer opening of the shell or at or close to the inner end of the shell.

Further preferred embodiments of the invention are defined by the dependent claims. In the following, examples of the invention will be illustrated by referring to the attached drawings.

These and further objects, features and advantages of the present invention will become apparent from the following description when taken in connection with the accompanying drawings which, for purposes of illustration only, show several embodiments in accordance with the present invention.

Figure 2:
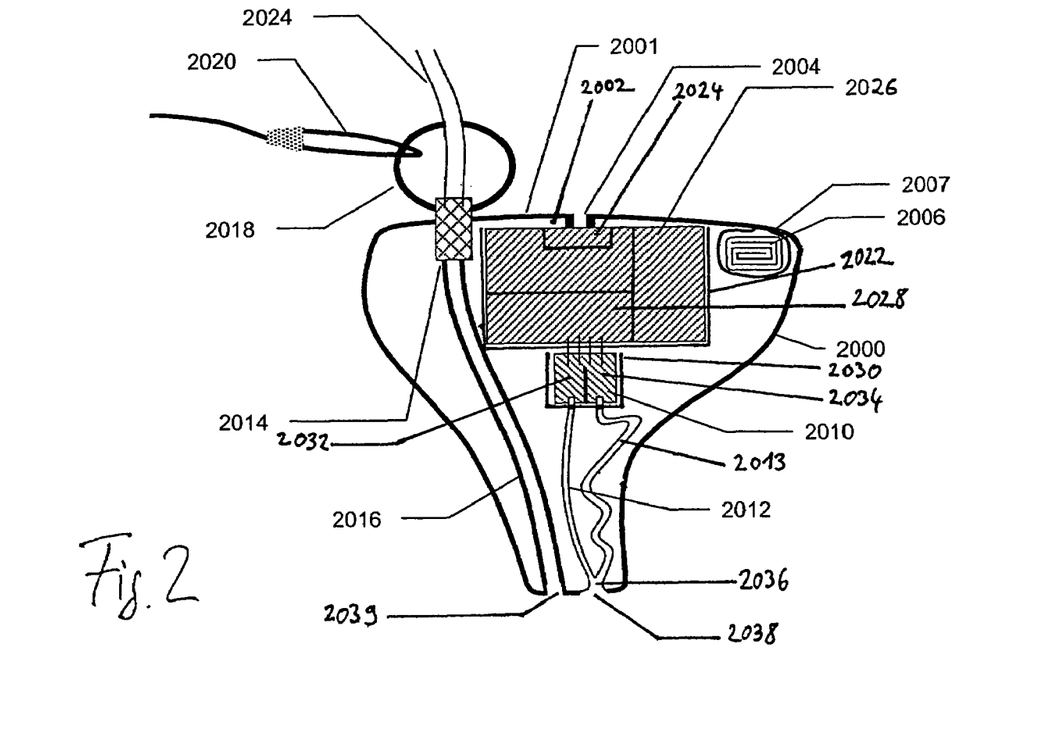
FIG. 2 is a view like FIG. 1, with an example of a hearing protection device according to the invention being shown.

FIG. 2 shows a hearing protection earplug comprising a hard shell 2000 which has preferably an elasticity of shore D85 to shore D65 and which has been formed by an additive build-up process (also known as "rapid prototyping"), for example, by layer-by-layer laser sintering of a powder material such as polyamide. A detailed description regarding examples of additive build-up processes for shells for hearing devices is to be found, for example, in U.S. Pat. No. 6,533,062 B1, so that this process need not be further described here.

The shape of the outer surface of the shell 2000 is individually adapted to the inner shape of the user's ear canal and outer ear for optimized fit of the earplug at the user's outer ear and in the user's ear canal. At least the distal portion of the shell 2000 (the lower portion in FIG. 2) is to be worn within the user's ear canal while the proximal portion may be worn also in the ear canal ("in-the-ear" configuration) or it may extend into the outer ear of the user. Prior to manufacturing the shell 2000, the inner shape of the user's ear canal and outer ear is measured, for example, by three-dimensional laser scanning or by taking an impression which then undergoes three-dimensional laser scanning. The three-dimensional data obtained in this way is used to determine the outer shape of the shell 2000 for the manufacturing process. Examples for such procedures are found, for example, in the above-mentioned U.S. Pat. No. 6,533,062 B1. In addition to customizing the outer shape of the shell 2000, which serves to optimize the fit of the shell 2000 within the user's ear canal and outer ear, thereby enhancing wearing comfort and retention of the earplug, the use of an additive build-up process for manufacturing the shell 2000 creates the option to also individually define mechanical structures in the interior of the shell 2000 as will be explained in the following.

The shell 2000 is provided at its outer end with an outer sound inlet opening 2004 and with a receptacle 2022 for receiving an electronic module 2002 with active elements including a microphone 2024 serving as an electroacoustic input transducer for converting ambient sound arriving at the outer opening 2004 into audio signals, an audio signal processing unit 2028 which usually comprises a digital signal processor, and a battery 2026 serving as a power source. The audio signal processing unit 2028 may act as an amplifier and may include some electronic filters, in particular digital filters, for example, for selecting speech signals over background noise. Usually the electronic module 2002 includes further elements, such as a volume control element, a pushbutton and a programming interface (these additional elements are not shown in FIG. 2).

The receptacle 2022 is designed to provide for a hard mounting of the electronic module 2002 at the shell 2000, i.e. without elastic or resilient materials being interposed. The electronic module 2002 may be mounted within the receptacle 2022 by exerting pressure on the electronic module 2002 in order to force it into the receptacle 2022. Alternatively the electronic module 2002 may be fixed within the receptacle 2022 by an adhesive.

The outer end of the shell 2000 is formed by a faceplate portion 2001 in which the sound inlet opening 2004 is provided. The sound inlet opening 2004 also may serve for manually operating the control element of the electronic module 2002.

Further, the shell 2000 is formed with a receptacle 2030 for an electroacoustic output transducer unit 2010 for converting audio signals processed by the audio signal processing unit 2028 into sound output. In the embodiment shown in FIG. 2, the output transducer unit 2010 comprises two separate acoustic outputs 2032 and 2034 in order to form a wideband receiver (in the example two-way receiver is shown) for improving the quality of the sound output from the output transducer unit 2010. The separate outputs usually will be formed by two physically distinct transducers 2032, 2034 mounted together or integrated together in a common unit in order to form the output transducer unit 2010.

The output transducers 2032 and 2034 may be of the same type (i.e. with the same resonance function) or of different types (i.e. with differing resonance functions). The output transducer unit 2010 may also comprise more than two output transducers.

The output transducer unit 2010 is hard mounted within the receptacle 2030 in a similar manner than the electronic unit 2002 in the receptacle 2022, for example, by press-fitting or by an adhesive which preferably is relatively hard and has an elasticity from shore D85 to shore D65. In particular, if the output transducer unit 2010 is mounted by press-fitting, assembly of the earplug in this respect is particularly easy. In addition, due to the fact that the output transducer unit 2010 is hard mounted within the receptacle 2030 the position of the output transducer unit 2010 within the shell 2000 is precisely and reliably defined. As will be explained later, this may help to optimize the acoustic properties of the earplug.

It is to be noted that despite the hard mounting of the electronic unit 2002 and the output transducer unit 2010 within the corresponding receptacles 2022 and 2030, respectively, no feedback problems between the output transducer(s) 2032, 2034 and the microphone 2024 occur, since in an active hearing protection earplug the total amplification is negative.

Each output transducer 2032, 2034 is connected with a separate sound output tube 2012, 2013, which merge into a common sound outlet tube 2036 leading to a sound outlet opening 2038 at the inner end of the shell 2000. The sound output tubes 2012, 2013 hence serve to mix the sound output of the output transducers 2032, 2034, thereby forming a passive crossover network for the sound output. The acoustic parameters of this passive crossover network can be adjusted by correspondingly shaping and/or sizing the sound output tubes 2012, 2013. In particular, each sound output tube 2012, 2013 can be adapted to the frequency response of the associated output transducer 2032 and 2034, respectively, in order to achieve a desired sound frequency response of the entire output transducer unit 2010. In particular, it is thereby possible to tune this frequency response as desired. The geometric parameters used in this respect may be the shape and length of the sound output tubes 2012, 2013 and the point where they merge into the common sound outlet tube 2036. Preferably each sound output tube 2012, 2013 is formed as a cavity integral within the shell 2000. Usually the acoustic properties of the sound output tubes 2012, 2013 are different from each other.

Such frequency tuning by shaping and/or sizing the sound output tubes 2012, 2013 by intention in order to achieve a desired sound frequency response not only can be used for a multi-way output transducer unit with at least two output transducers, but rather applies also generally to the case in which there is only one output transducer and/or only one sound output tube.

The general concept of frequency tuning in an earplug, which in general not only applies to active hearing protection earplugs but also to hearing aids, may comprise the following steps: First a desired sound frequency response function of the output transducer(s) is determined, when mounted within the shell; and an acoustic model of the shell including the output transducer(s) is established. Then the shell is formed with a sound cavity comprising at least one sound outlet tube for the output transducer(s), which is shaped and sized according to the model in order to tune the sound frequency response of the output transducer(s) according to the desired sound frequency response. Thereby, for example, an undesired frequency response of the acoustic output transducer may be corrected at least to some extent by an appropriate design of the sound output tube(s). For example, typical hearing aid receivers have a quite sharp shape of the frequency response, which in some cases may be even beneficial for hearing aid applications due to the low power request of such receivers. For an active hearing protection application, however, where natural hearing impression will become more an issue than maximum output power, an appropriate sizing/shaping of the sound output tubes may help to shape and/or tune the frequency response of the output transducer(s) to achieve the requests for an active hearing protection device.

According to one embodiment, the desired sound frequency response function and the acoustic model relate to the shell when worn in a standard ear canal (and outer ear); i.e. in this case the specific shape of the actual user's ear is not considered.

However, since the statistical spread of individual ear shapes is significant and since the shape of the user's ear canal affects the actual sound frequency response of the output transducer(s), a user-optimized sound output can be achieved, if the inner shape of the user's outer ear and ear canal is measured before manufacturing of the earplug and if the desired sound frequency response and the acoustic model is related to the shell when worn in the measured user's ear canal and outer ear. As a result, the sound cavity, i.e. the sound output tube(s), is individually shaped and sized according to the measured user's ear canal and outer ear. Thus, the sound frequency response of the output transducer(s) can be individually optimized.

The acoustic model may include parameters such as the position of the output transducer(s) (i.e. the position of the corresponding receptacle), the frequency response of the output transducer(s) and the three-dimensional information on a user's ear as measured. In this respect it is beneficial if the position of the output transducer(s) is precisely defined by hard mounting the output transducer(s) within the shell.

It has to be noted that for a customized earplug it is already necessary for determining the outer shape of the shell 2000 to measure the inner shape of the user's ear canal and outer ear. Hence, these data are already available for a customized earplug and therefore can be entered without additional efforts into the acoustic model of the earplug for individually optimizing the sound output.

The shell 2000 also may comprise a measurement channel 2016 formed as a cavity integral with the shell 2000 and extending from the outer end of the shell 2000, i.e. the faceplate 2001, through the shell 2000 to the inner end of the shell 2000 having a sound opening 2039, wherein the measurement channel 2016 comprises at its outer end means 2014 for being acoustically connected to an external measurement unit (not shown) via an external in-situ measurement probe tube 2024.

In the embodiment shown in FIG. 2, these connection means 2014 form a multi-purpose cord adapter, an example of which is shown in more detail in FIGS. 5 to 8. The outer end of the measurement channel 2016 terminates an opening in the faceplate 2001 within which an adapter element 2014 is provided which may form a adapter element in the form of a hollow, generally cylindrical sleeve 22 which is inserted into and fixed in the opening 20 in a permanent manner, for example by cementing. However, it may also be provided in a removable manner or as a part of the faceplate 2001. In order to detachably connect to the measurement tube 2024, the adapter element 2014 may comprise a thread 24 for connecting to a corresponding mating thread 27 at the end of the measurement tube 2024. The measurement channel 2016, when connected to the measurement tube 2024 by the fitting element 2014, allows for providing sound measurements at the inner end of the shell 2000 so that, for example, the actual sound attenuation of the earplug, when inserted into the user's ear canal, can be directly measured. For an active hearing protection earplug, the measurement channel 2016 also may serve to measure the performance of the electronic unit 2002 and the output transducer unit 2010 when the earplug has been inserted into the user's ear canal. In addition, the output transducer unit 2010 and the microphone 2024 may be used as built-in measurement equipment.

When the measurement channel 2016 is not used, the measurement tube 2024 is removed from the adapter element 2014 and the opening of the adapter element 2014 can be closed by a threaded plug 40 which may, for example, include means 42, 44 for fixing a neck cord 2020 to the earplug. Alternatively, the adapter element 2014 may comprise such means for fixing the neck cord 2020, for example, a cord fixation ring 2018.

Alternatively, the opening of the adapter element 2014 may be closed by a threaded plug 28 which may include additional functions, such as communication functions. In particular, the threaded plug 28 may include a RFID-tag.

In some applications, the measurement channel may terminate already within the interior of the shell for enabling measurements at cavities within the shell.

Many applications for hearing protection devices experience strong variation in noise exposure over time. An extreme example is when people are shooting with guns, e.g. hunters or soldiers, where speech communication in-between the actions is strongly desired and where the sound may become very loud for short time periods. In active hearing protection devices such conditions have been addressed by so-called "peak clippers" which are very easy to implement in the audio signal processing unit and which limit the sound output of the device independent of the input signal while leaving the signal undistorted for normal noise levels. The present invention addresses the option to provide for such peak clipping independent of an electronic audio signal processing unit so that it may be applied also to passive hearing protection devices.

This can be achieved by providing for a mechanical peak clipper unit, i.e. mechanical closing means which are adapted to acoustically close a sound passage for the hearing protection device leading to the user's inner ear canal, if the sound pressure level exceeds a threshold value and to acoustically open the sound passage as long as the sound pressure level does not exceed the threshold value. In the case that the sound passage extends throughout the shell of the earplug, i.e. from an outer opening of the shell to the inner end of the shell, the peak clipper closing means may be provided at or close to the outer end of the sound passage or at or close to the inner end of the sound passage. In case that the sound passage extends, in an active hearing protection device, from the output transducer(s) to the inner end of the shell, the peak clipper closing means will be located at or close to the inner end of the sound passage. Preferably, the closing means are formed integral with the shell.

Preferably, the closing means include a closing element, for example, a lid-like or valve-like structure, which is adapted to engage, if exposed to a sound pressure above the threshold value, on a mating counter-element, which may be designed as some kind of valve seat, in order to close the sound passage, wherein the closing element is biased away from the counter-element.

Figure 3:
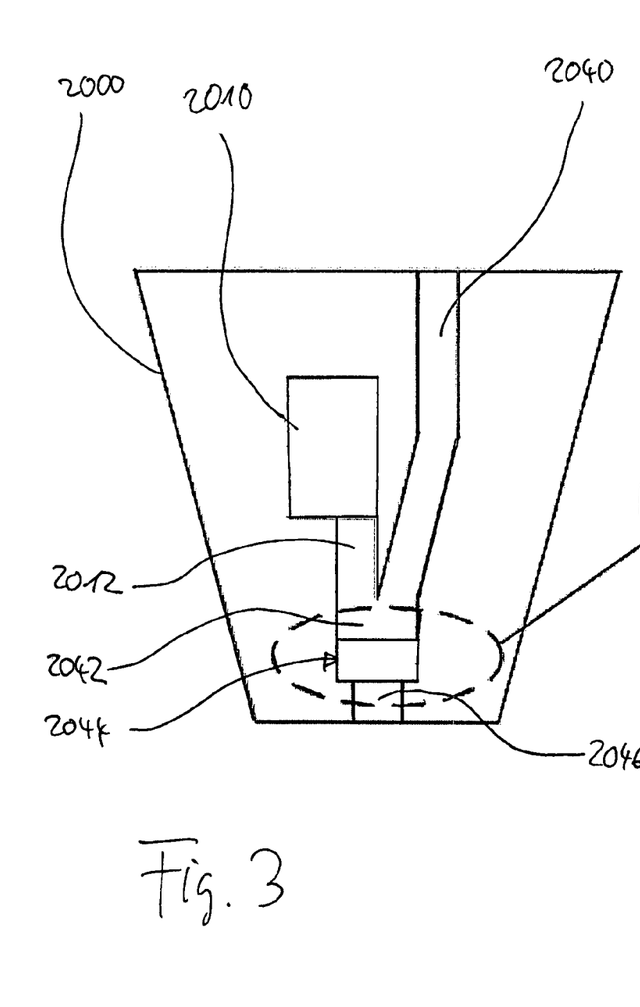
FIG. 3 is a view like FIG. 2, with a schematic modified embodiment of an active hearing protection earplug being shown.
Figure 4:
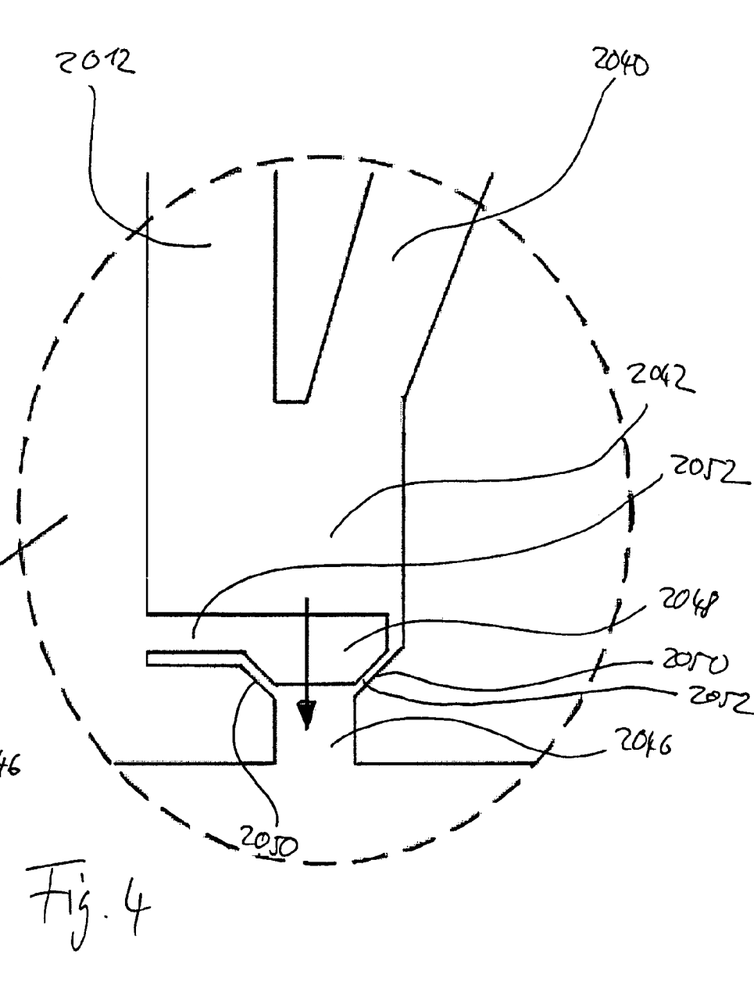
FIG. 4 is an enlarged view of the distal end of the earplug of FIG. 3.
Figure 5:
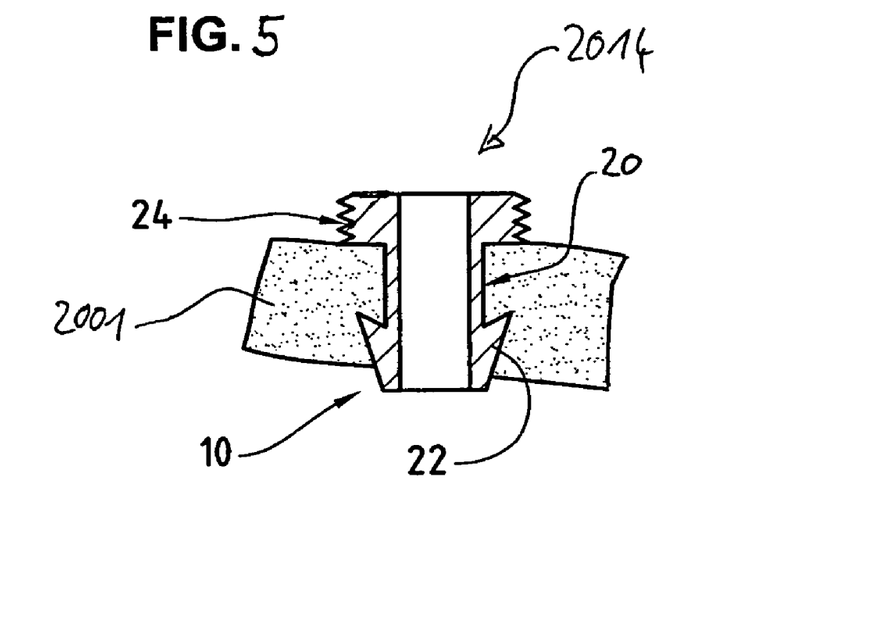
FIGS. 5 to 8 longitudinal sectional views of an example of the multi-purpose cord adapter to be used in the embodiment of FIG. 1 or 2 in different modes of operation.
Figure 6:
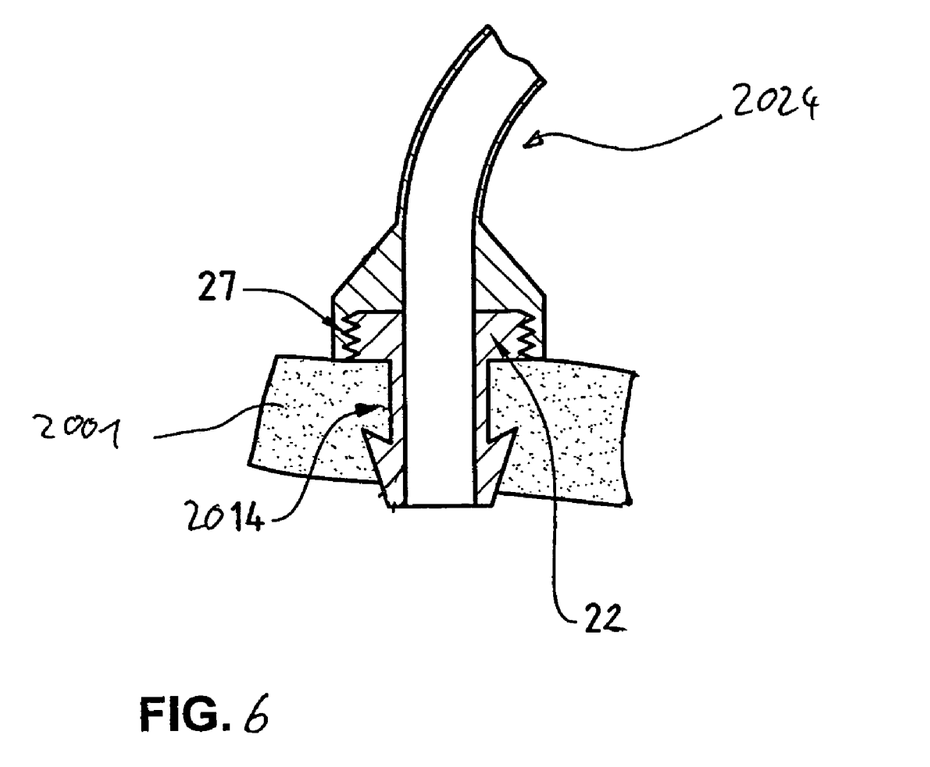
Figure 7:
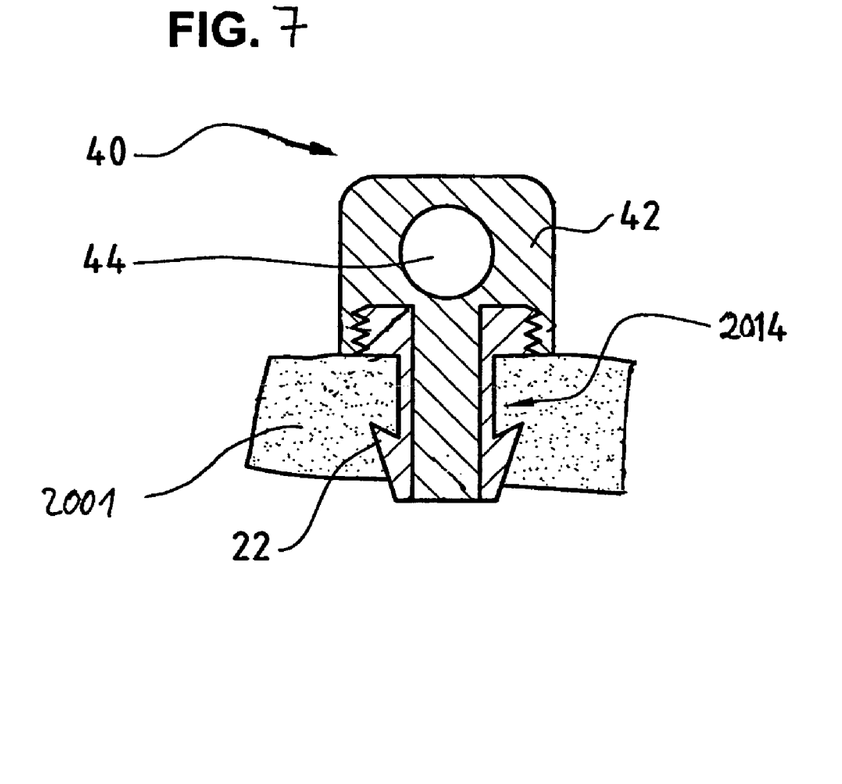
Figure 8:
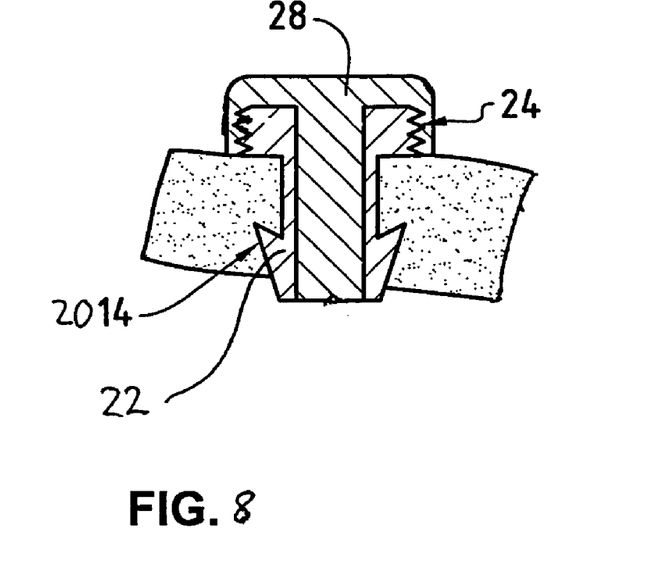

An example of such a construction is shown in FIG. 3 and 4, wherein an active hearing protection earplug is schematically shown which comprises an output transducer unit 2010, a sound output channel 2012 and a venting channel 2040 which merges with the sound output channel 2012 into a common sound output channel 2042. The venting channel 2040 starts at the outer end of the shell 2000. At the inner end of the common sound output channel 2042 a closing element 2048 which is designed like a lid is formed integral with the shell 2000. The closing element 2048 is connected with the shell 2000 by an integral holding portion 2052 which serves to bias the closing element 2048 away from a mating counter-element 2050 which is likewise formed integral with the shell 2000. The counter-element 2050 is designed like a valve seat and has an opening which forms an inner sound outlet channel 2046 at the inner end of the shell 2000.

In the position shown in FIG. 4, the closing element 2048 is in its open position, in which a gap 2054 is left between the lower side of the closing element 2048 and the counter-element 2050, which serves as a sound passage for sound waves travelling from the common outlet channel 2042 to the inner sound outlet channel 2046.

If the sound pressure level within the common sound channel 2042 exceeds a threshold value which is primarily defined by the design of the holding portion 2052 the closing element 2048 is forced towards the counter-element 2050 by pressure action (see arrow in FIG. 4) so far that the lower side of the closing element 2048 will rest on the counter-element 2050, thus closing the sound passage gap 2052, whereby sound transmission to the inner outlet channel 2046 is prevented. Thereby it can be prevented that the user's inner ear canal experiences excessive sound pressure levels.

Figure 1:
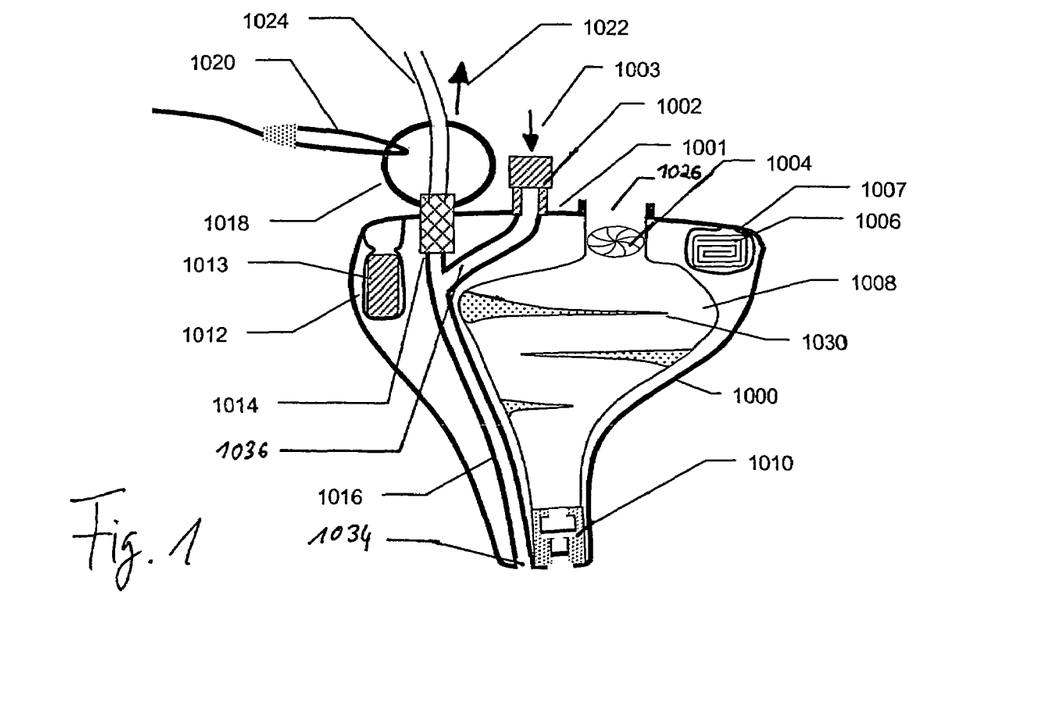
FIG. 1 shows a schematic longitudinal sectional view of a passive hearing protection earplug according to the invention.

FIG. 1 shows an example of a passive hearing protection earplug comprising a customized hard shell 1000 which may be manufactured essentially in the same manner as the shell 2000 of the earplug of FIG. 2.

Similar to the embodiment of FIG. 2, the shell 1000 of FIG. 1 includes an integrated measurement channel 1016 with an adapter element 1014. According to FIG. 1, the shell 1000 comprises an outer sound inlet opening 1026 which leads into a resonance cavity 1008 with means 1030 for resonance frequency tuning. The inner end of the resonance cavity or chamber 1008 is formed by an acoustic filter 1010 which serves to provide for a defined sound attenuation through the shell 1000. The outer end of the resonance cavity 1008 is provided with a mechanical peak clipper closing means 1004 which may have a similar construction and function as the closing means 2044 shown in FIG. 2. The closing means 1004 serve to acoustically close the outer sound inlet opening if the sound pressure level exceeds a given threshold value.

FIGS. 1 and 2 show an example of a passive hearing protection earplug and an active hearing protection earplug, respectively, wherein some features are combined which may be advantageously implemented by manufacturing the shell of the earplug by an additive build-up process, such as layer-by-layer laser sintering.

The earplug of FIG. 1 includes, in addition to the features already described above, a faceplate 1001 at the outer end of the shell 1000. The faceplate 1001 includes the outer sound input opening 1026 provided with the mechanical peak clipper 1004, a multi-purpose cord adapter element 1014 with an in-situ measuring hole for optionally connecting the measuring hole to an external measuring tube 1024 or to a plug for closing the measuring hole in the normal operation of the earplug, and a sound inlet opening which is provided with a button 1002 which is manually operable in the direction 1003 to act as an attenuation button closing the sound inlet opening or as communication button opening the sound inlet opening for sound input into a sound passage 1036 which merges at its distal end with an in-situ measuring channel or tube 1016 which is acoustically connected to the measuring hole in adapter element 1014 and which extends to an inner sound opening 1034 at the inner end of the shell 1000. The sound input opening 1026 communicates with the resonance cavity 1008 which is provided with an inner mechanical structure 1030 for frequency tuning. At the distal end of the resonance cavity 1008 a semi-integrated passive acoustic filter 1010 is provided. The tubes 1036 and 1016 are formed integral with the shell 1000. Further, also an insert cavity 1007 for a RFID (radio frequency identification device)-tag 1006 and an insert cavity 1012 for a detectable metal part 1013 are formed integral with the shell 1000. At the adapter element 1014 or at the plug for closing the measuring hole of the adapter element a cord fixation ring 1018 may be provided for fixing a neck cord 1020 at the shell 1000 for preventing loss of the earplug. The ring 1018 or the cord 1020 also may serve to manually pull the earplug in the axial direction 1022.

The earplug of FIG. 2 includes, in addition to the features already described above, a cord fixation ring 2018, a neck cord 2020 and a cavity 2007 for a RFID-tag 2006, which are similar to the corresponding components of the earplug of FIG. 1.

In the following, the additional features and functions of the earplugs of FIGS. 1 and 2 will be explained in more detail.

Multipurpose Cord Adapter

In order to confirm acoustical performance of an HPD, an in-situ measurement tube is implemented to allow measurement of attenuation when the individual wears the device. Naturally this tube needs to be closed off during normal operation. The core element of this tube is the faceplate component referred to a multipurpose cord adapter 1014, 2014 that embodies several functions and features: fixation of external in-situ measurement probe tube 1024, 2024, one possible holder of the cord fixation ring 1018, 2018 for the neck cord 1020, 2020, holder of an ergonomic pull means (e.g. the cord fixation ring 1018, 2018) for an inverse anatomy switch, holder of a plug for closing the in-situ tube during normal operation. If the element is made of metal it can serve as a metal component for detection purposes 1013 which in that case spares an extra insert cavity 1012. The design of the multipurpose cord adapter element 1014, 2014 is given extensive freedom (shape, material, insertion/removal concept, etc.) due to the base technology used for the faceplate portion of the earplug 1001, 2001.

Semi-Integrated Passive Filter

In passive HPDs acoustical filters mainly serve two purposes: firstly there is the defined amount of attenuation, secondly the filter can shape the frequency response of the attenuation in order to protect some frequencies while letting others through (e.g. block low frequency noise and let speech pass above 1 kHz). The proposed base technology enables both usages of predefined component placement geometries (e.g. cavities 1012 for metal component 1013 insertion) as well as semi-integration of functions where the material itself becomes part of the solution (e.g. insert cavities, acoustical filters). The semi-integrated passive filter 1010 is a structure of the second kind, where the tubes are made in shell material while the membranes are inserted components. Selection of membranes can be done to order and individual need, hence the component remains customizable. The filter must be considered and dimensioned together with other filter means like the customizable front chamber shaping structure (or resonance cavity) 1008, 1030 (Helmholtz resonator) and the mechanical peak clipper 1004.

Communication/Attenuation Button

A core function of a passive HPD is to enable temporary audio bypass for purposes like listening to speech, alarm or other desired audio signals even though they are mixed with loud noise. This is often performed by a push/return-button opening a tube either bypassing the filter of the system or leading into the in-situ measurement probe tube 1016 on the inside of the closing plug to be connected to the adapter element 1014 when the measuring tube 1024 is removed. The integration of such a device into the faceplate 1001 overcomes many drawbacks of similar standard component solutions (e.g. complex tubing, acoustical leakage). An even more integrated solution is achieved by building the switch directly into the multipurpose cord adapter core element 1014 replacing the sealing plug. If the button is made of metal it could serve as a metal piece for the detection function, thereby eliminating the need for the separate metal part 1013.

Inverse Anatomy Force Button

A further level of integration of the on/off switch is based on the shell technology combined with the natural anatomy of the outer ear. In addition to a defined audio "leak" via a tube 1016 through the HPD, there is the alternative of creating a temporary leak between the device and the outer ear by slightly pulling the device out of the ear. This pull can be done by the cord 1020 or directly by grip and pull on the cord ring 1018. If the shell 1000 is shaped in an appropriate manner, the ear shape is such that the device will be naturally pulled back in place when the pull is relaxed.

Intelligent Passive HPD

Inserting a device into the ear principally blocks the acoustical tube (ear canal) and destroys the natural outer ear amplification and frequency shaping (open ear gain, OEG). The open ear has a natural resonance in the frequency area of the most critical speech information, hence this loss is a real loss and not normally desired. The resonance frequency is given by the length of the tube; hence there is a need for compensation of the reduced length. This can be individually modeled and implemented with a defined acoustical front (outer) chamber 1008 and artificially stretched to a desired length by a mechanical means 1030 for resonance shaping directly integrated into the shell making process, possibly in combination with frequency shaping filter 1010 and means for maximum power limiting such as a mechanical peak clipper 1004.

Detectable HPD

HPDs are mostly used in industrial environments. In the food processing industry an additional requirement also affects these devices. Any foreign particle (to the food ingredients) must be detectable within the production process. For HPDs this implies that the devices need to contain a certain amount of metal to enable the detection equipment to find it if lost in the production line. Metal can be inserted into HPDs in a number of different ways: for active devices there should be enough metal in the transducers 2002, 2010 and the battery contained in 2002, hence no additional component is needed. In case of passive devices metal can be mixed into the shell base material 1000, a specific metal component 1013 can be mounted in a prepared cavity 1012, the cord adapter faceplate element 1014 can be made of metal and the button part of the on/off switch 1002 can be made of metal. In a HPD with a RFID tag, the tag itself is detectable if the equipment for detection is implemented in the production line.

HPD Wearing Compliance

Wearing of HPDs in industrial environments obliges to regulations in most countries. Assuming that the devices have the desired protective effect when they are worn (most other topics described address this very issue), the wearing itself becomes the compliance control topic. With recent developments in miniaturized RFID (radio frequency identification devices) technology, it becomes feasible to implement such devices into a customized HPD given the shell technology described. The RFID tag 1006, 2006 is inserted into a predefined cavity 1007, 2007 and when the wearer passes through gateways equipped with RFID detection systems, the positions of the two HPDs can be obtained and the control function carried out according to whether a predefined condition regarding the detected positions is fulfilled or not (e.g. separation of the HPDs according to the width of the head and height of the HPDs according to the ear height). As mentioned, the RFIDs can also serve as HPD detection devices in food production processes.

Basic Functions

Functions that conventionally are mounted components, such as a grip handle for insertion and removal of the HPD, can easily be integrated with use of the shell technology. The product design and assembly more and more becomes a software issue and the individual product is increasingly designed to order according to the specific requirements of each customer.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A method for manufacturing an earplug including a shell to be worn at least in part in a user's ear canal and an acoustic output transducer unit, mounted within said shell, for sound output at an inner end of said shell, comprising: determining a desired sound frequency response function of said output transducer unit when mounted within said shell, establishing an acoustic model of said shell including said output transducer unit, and forming a shell having a receptacle for mounting said output transducer unit within said shell and a sound cavity connecting said output transducer unit to a sound outlet opening at said inner end of said shell, wherein said sound cavity is shaped and sized according to said model in order to tune an actual sound frequency response of said output transducer unit according to said desired sound frequency response of said output transducer unit.

2. The method of claim 1, wherein said desired sound frequency response function and said model relate to said shell when worn in a standard ear canal and outer ear.

3. The method of claim 1, wherein further comprising: measuring an inner shape of said user's outer ear and ear canal, wherein said desired sound frequency response function and said model relate to said shell when worn in the measured user's ear canal and outer ear, with said sound cavity thus being individually shaped and sized according to said measured inner shape of said user's ear canal and outer ear.

4. The method of claim 1, wherein said output transducer unit comprises two separate outputs, wherein said sound cavity has a Y-like shape with a first sound output tube and a second sound output tube combining at a mixing point into a common sound outlet tube which connects to said sound outlet opening, and wherein said first sound output tube connects to one of said outputs of said output transducer unit and said second sound output tube connects to the other one of said outputs said output transducer unit.

5. The method of claim 1, wherein said earplug is designed as an active hearing protection device including an input transducer and an audio signal processing unit, wherein amplification of an active system comprising said input transducer, said audio signal processing unit and said output transducer unit is negative.

* * * * *